United States Patent [19]

Häbich et al.

[11] Patent Number: 5,424,426
[45] Date of Patent: Jun. 13, 1995

[54] DITHIOLANYLGLYCINE-CONTAINING HIV PROTEASE INHIBITORS OF THE HYDROXYETHYLENE ISOSTERE TYPE

[75] Inventors: Dieter Häbich; Wolfgang Bender; Jutta Hansen, all of Wuppertal; Arnold Paessens, Haan, all of Germany

[73] Assignee: Bayer Aktiengesellschaft, Leverkusen, Germany

[21] Appl. No.: 59,488

[22] Filed: May 10, 1993

[30] Foreign Application Priority Data

May 14, 1992 [DE] Germany .......... 42 15 874.5

[51] Int. Cl.⁶ .................................. C07K 5/02
[52] U.S. Cl. ................. 544/124; 544/360; 544/365; 546/169; 546/194; 546/273; 546/284
[58] Field of Search ............... 546/169, 194, 273, 284; 544/124, 360, 365

[56] References Cited

U.S. PATENT DOCUMENTS

| | | |
|---|---|---|
| 5,095,006 | 3/1992 | Bender et al. .......... 546/156 |
| 5,145,951 | 9/1992 | Voges et al. .......... 546/156 |
| 5,162,538 | 11/1992 | Voges et al. .......... 546/156 |

FOREIGN PATENT DOCUMENTS

| | | |
|---|---|---|
| 0357332 | 3/1990 | European Pat. Off. . |
| 0393445 | 10/1990 | European Pat. Off. . |
| 0402646 | 12/1990 | European Pat. Off. . |
| 0403828 | 12/1990 | European Pat. Off. . |
| 0434365 | 6/1991 | European Pat. Off. . |
| 0437729 | 7/1991 | European Pat. Off. . |
| 0438311 | 7/1991 | European Pat. Off. . |
| 0443559 | 8/1991 | European Pat. Off. . |
| 0443560 | 8/1991 | European Pat. Off. . |
| 0443573 | 8/1991 | European Pat. Off. . |
| 0445467 | 9/1991 | European Pat. Off. . |
| 0446485 | 9/1991 | European Pat. Off. . |
| 0456185 | 11/1991 | European Pat. Off. . |
| 0459465 | 12/1991 | European Pat. Off. . |
| 9009191 | 8/1990 | WIPO . |
| 9012804 | 11/1990 | WIPO . |
| 9106561 | 5/1991 | WIPO . |
| 9110442 | 7/1991 | WIPO . |
| 9210509 | 6/1992 | WIPO . |
| 9210510 | 6/1992 | WIPO . |

OTHER PUBLICATIONS

Joel R. Huff, "HIV Protease: A Novel Chemotherapeutic Target for AIDS", *Journal of Medicinal Chemical*, vol. 34, No. 8, pp. 2304–2314 (Aug., 1991).

J. Hansen et al., "Partial Purification ... Antibody", *The EMBO Journal*, vol. 7, No. 6, pp. 1785–1791 (1988).

R. Pauwels et al., "Rapid and automated ... anti-HIV compounds", *Journal of Virological Methods*, 20, pp. 309–321 (1988).

P. Buhlmayer et al., "Synthesis and Biological ... Human Renin", *J. Med. Chem.*, 31, pp. 1839–1846 (1988).

D. J. Plata, et al., "The Stereospecific ... Template", *Tetrahedron Letters*, vol. 32, No. 30, pp. 3623–3626 (1991).

D. H. Rich, et al., "L-687,908, a Potent ... Inhibitor", *J. Med. Chem.*, 34, pp. 1225–1228 (1991).

M. P. Mertes et al., "w-Dithiolano Amino Acids", *J. Med. Chem.*, 12, pp. 342–343, (1969).

*Primary Examiner*—Robert Gerstl
*Attorney, Agent, or Firm*—Sprung Horn Kramer & Woods

[57] ABSTRACT

The invention relates to dithiolanylglycine-containing HIV protease inhibitors of the hydroxyethylene isostere type of the general formula (I)

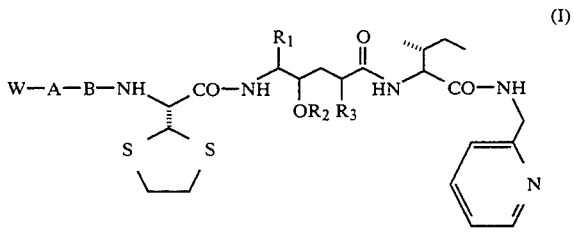

processes for their preparation and their use as retroviral agents.

3 Claims, No Drawings

DITHIOLANYLGLYCINE-CONTAINING HIV PROTEASE INHIBITORS OF THE HYDROXYETHYLENE ISOSTERE TYPE

The invention relates to dithiolanylglycine-containing HIV protease inhibitors of the hydroxyethylene isostere type, processes for their preparation and their use as retroviral agents.

It has already been attempted to employ peptides and pseudopeptides, which in some cases also have renin inhibitor activity, in combating AIDS [cf. WO 91/06561; WO 90/09191; WO 90/12804; EP 393 445; EP 402 646; EP 373 576; WO 91/06501; EP 459 465 and EP 437 729].

The present invention relates to dithiolanylglycine-containing HIV protease inhibitors of the hydroxyethylene isostere type of the general formula (I)

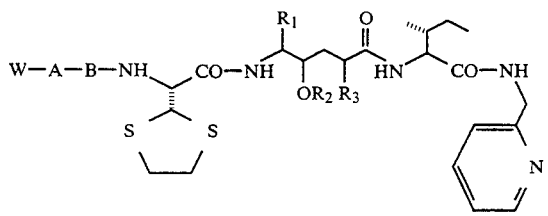

in which
W represents hydrogen or a typical amino protective group, or represents a group of the formula $R^4$—CO—,
in which
$R^4$ denotes quinolyl, indolyl, pyridyl, morpholino or piperazinyl, or denotes a radical of the formula

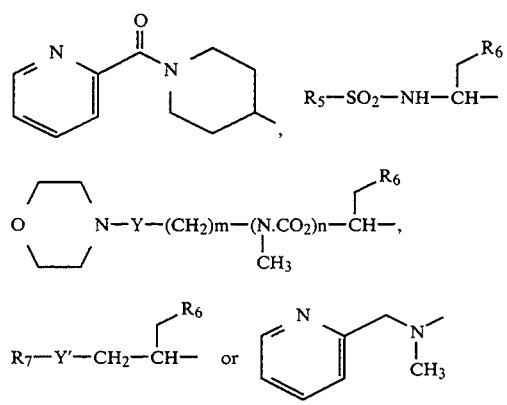

in which
$R^5$ denotes straight-chain or branched alkyl having up to 14 carbon atoms, which is optionally substituted by phenyl or naphthyl, or denotes benzyloxy or aryl having 6 to 10 carbon atoms, which is in turn substituted by alkyl having up to 4 carbon atoms, or denotes morpholino or pyrrolidinyl bonded via N,
$R^6$ denotes phenyl or naphthyl,
$R^7$ has the abovementioned meaning of $R^5$ but does not represent morpholino or pyrrolidinyl bonded via N,
Y and Y' independently of one another denote the CO or $SO_2$ group, m denotes a number 0, 1 or 2,
n denotes a number 0 or 1,
A and B are identical or different and represent a direct bond or represent a radical of the formula

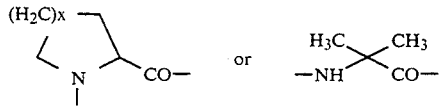

in which
x denotes the number 1 or 2 or
represent a group of the formula

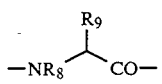

in which
$R^8$ denotes hydrogen or straight-chain or branched alkyl having up to 4 carbon atoms,
$R^9$ denotes cycloalkyl having 3 to 8 carbon atoms or aryl having 6 to 10 carbon atoms or hydrogen, or denotes straight-chain or branched alkyl having up to 8 carbon atoms,
where the alkyl is optionally substituted by cyano, methylthio, hydroxyl, mercapto or guanidyl or by a group of the formula —$NR^{10}R^{11}$ or $R^{12}$—OC—,
in which
$R^{10}$ and $R^{11}$ independently of one another represent hydrogen, straight-chain or branched alkyl having up to 8 carbon atoms or phenyl, and
$R^{12}$ denotes hydroxyl, benzyloxy, alkoxy having up to 6 carbon atoms or the abovementioned group —$NR^{10}R^{11}$, or the alkyl is optionally substituted by cycloalkyl having 3 to 8 carbon atoms or by aryl having 6 to 10 carbon atoms, which is in turn substituted by hydroxyl, halogen, nitro, alkoxy having up to 8 carbon atoms or by the group —$NR^{10}R^{11}$,
in which
$R^{10}$ and $R^{11}$ have the abovementioned meaning, or the alkyl is optionally substituted by a 5- or 6-membered nitrogen-containing heterocycle or indolyl, in which the corresponding —NH functions are optionally protected by alkyl having up to 6 carbon atoms or by an amino protective group,
$R^1$ represents straight-chain or branched alkyl having up to 3 carbon atoms, which is substituted by cyclohexyl or phenyl,
$R^2$ represents hydrogen or straight-chain or branched alkyl having up to 4 carbon atoms, or represents a hydroxyl protective group,
$R^3$ represents straight-chain or branched alkyl or alkenyl each having up to 6 carbon atoms or represents benzyl,
and their physiologically acceptable salts.

The compounds of the general formula (I) according to the invention have a number of asymmetric carbon atoms. They can be present independently of one another in the D- or L-form. The invention includes the optical antipodes, as well as the isomer mixtures or racemates. The groups A, B and D are preferably present independently of one another in the optically pure form, preferably in the L-form.

The radical of the general formula (II)

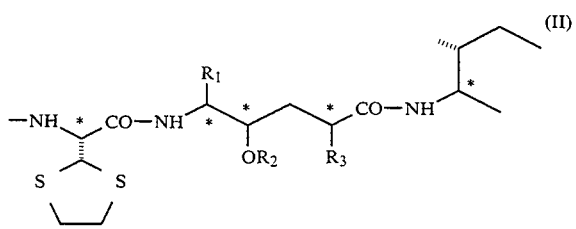

has 5 asymmetric carbon atoms (*). They can be present independently of one another in the R- or S-configuration.

Amino protective groups in the context of the invention are the customary amino protective groups used in peptide chemistry.

These preferably include: benzyloxycarbonyl, 9-fluorenylmethyloxycarbonyl, methoxycarbonyl, tert-butoxycarbonyl, allyloxycarbonyl, vinyloxycarbonyl, 2-nitrobenzyloxycarbonyl, formyl, acetyl, 2,2,2-trifluoroacetyl, 2,2,2-trichloroacetyl, benzoyl or pyridylmethoxycarbonyl.

The compounds of the general formula (I) according to the invention can be present in the form of their salts. These can be salts with inorganic or organic acids or bases. Hydroxyl protective group in the context of the above-mentioned definition in general represents a protective group of the series: trimethylsilyl, triethylsilyl, triisopropylsilyl, tert-butyldimethylsilyl, tert-butyldiphenylsilyl, triphenylsilyl, trimethylsilylethoxycarbonyl, benzyl, triphenylmethyl (trityl), monomethoxytrityl (MMTr), dimethoxytrityl (DMTr), benzyloxycarbonyl, 2-nitrobenzyl, 4-nitrobenzyl, 2-nitrobenzyloxycarbonyl, 4-nitrobenzyloxycarbonyl, tert-butoxycarbonyl, allyloxycarbonyl, 4-methoxybenzyl, 4-methoxybenzyloxycarbonyl, formyl, acetyl, trichloroacetyl, 2,2,2-trichloroethoxycarbonyl, 2,4-dimethoxybenzyl, 2,4-dimethoxybenzyloxycarbonyl, methoxymethyl, methylthiomethyl, methoxyethoxymethyl, [2-(trimethylsilyl)ethoxy]methyl, 2-(methylthiomethoxy)ethoxycarbonyl, tetrahydropyranyl, benzoyl, 4-methylbenzoyl, 4-nitrobenzoyl, 4-fluorobenzoyl, 4-chlorobenzoyl and 4-methoxybenzoyl. Acetyl, benzyl and tert-butyldimethylsilyl are preferred.

Preferred compounds of the general formula (I) are those in which

W represents hydrogen, tert-butoxycarbonyl (BOC), 9-fluorenylmethoxycarbonyl (Fmoc), benzyloxycarbonyl (Z) or pyridylmethoxycarbonyl, or represents a group of the formula R$_4$—CO— in which

R$^4$ denotes quinolyl, indolyl, pyridyl, morpholino or piperazinyl, or denotes a radical of the formula

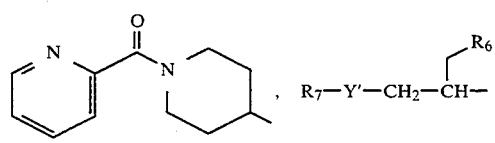

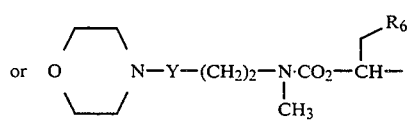

in which

R$^6$ denotes phenyl or naphthyl,

R$^7$ denotes straight-chain or branched alkyl having up to 8 carbon atoms, tolyl, benzyloxy, phenyl or naphthyl, A and B independently of one another represent a direct bond or represent proline, alanine, arginine, aspartic acid, asparagine, glutamic acid, glutamine, histidine, leucine, methionine, threonine, tyrosine, cysteine, glycine, isoleucine, lysine, phenylalanine, serine, tryptophan or valine, R$^1$ represents benzyl or methylcyclohexyl, R$^2$ represents hydrogen, R$^3$ represents straight-chain or branched alkyl or alkenyl each having up to 4 carbon atoms, or benzyl, and their physiologically acceptable salts.

Particularly preferred compounds of the general formula (I) are those in which

W represents hydrogen or tert-butoxycarbonyl (BOC) or represents a group of the formula R$^4$—CO—, in which R$^4$ denotes quinolyl or indolyl, or denotes a radical of the formula

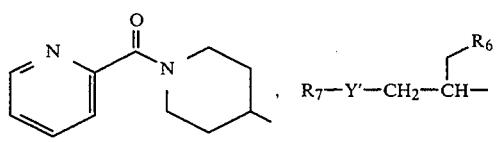

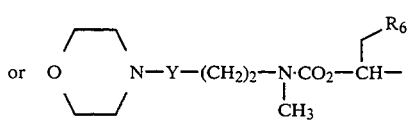

in which

R$^6$ denotes phenyl or naphthyl,

R$^7$ denotes straight-chain or branched alkyl having up to 4 carbon atoms, tolyl, benzyloxy, phenyl or naphthyl, Y and Y' independently of one another denote the CO or SO$_2$ group, A and B independently of one another represent a direct bond, or represent phenylalanine, R$^1$ represents benzyl or methylcyclohexyl, R$^2$ represents hydrogen, R$^3$ represents straight-chain or branched alkyl having up to 3 carbon atoms, allyl or benzyl, and their physiologically acceptable salts.

Processes for the preparation of the compounds of the formula (I) according to the invention have additionally been found, characterised in that

[A] in the case in which A and B represent a direct bond compounds of the general formula (III)

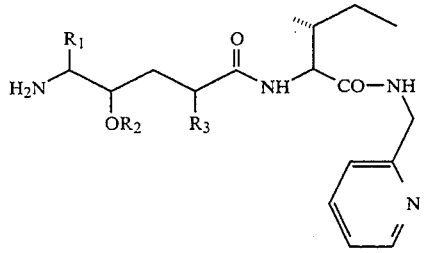 (III)

in which
R$^1$, R$^2$ and R$^3$ have the above-mentioned meaning,
are first reacted with compounds of the general formula (IV)

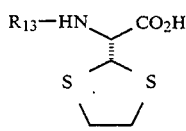 (IV)

in which
R$^{13}$ represents one of the above-mentioned amino protective groups, preferably Boc,
in inert organic solvents, in the presence of a base and of an auxiliary,
then the protective group R$^{13}$ is removed by the methods customary in peptide chemistry (W=H) and, in the case in which W≈H, the product is reacted in a last step with compounds of the general formula (V)

W'—X (V)

in which
W' has the above-mentioned meaning of W, but does not represent hydrogen and
X, depending on the particular meaning of the substituents mentioned above under W, represents hydroxyl or halogen,
likewise in organic solvents and in the presence of a base and of an auxiliary and
[B] in the case in which A and/or B does not represent a direct bond,
compounds of the general formula (III) are either reacted directly with compounds of the general formula (VI)

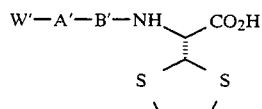 (VI)

in which
W' has the above-mentioned meaning and
A' and B' have the above-mentioned meaning of A and B but do not simultaneously represent a bond,
or are reacted successively first either with compounds of the general formula (VII)

R$_{13}$—A'—B'—NH⟨CO$_2$H, S—S⟩ (VII)

in which
R$^{13}$, A' and B' have the above-mentioned meaning,
in inert solvents and in the presence of a base and of an auxiliary,
then, with prior removal of the protective group R$^{13}$ as described under [A], the product is reacted with compounds of the general formula (V), or
compounds of the general formula (III) are first reacted with compounds of the general formula (IV) as described under [A], the protective group R$^{13}$ is removed, and in a last step the product is reacted with compounds of the general formula (VIII)

W'—AZ'—B'—OH (VIII)

in which
W', A' and B' have the above-mentioned meaning,
by the methods customary in peptide chemistry, if appropriate with activation of the carboxylic acid function and with prior deblocking of the amine function, in inert organic solvents and in the presence of a base and of an auxiliary,
and in the case in which W represents hydrogen, the protective group is removed as described under [A], and, if appropriate, a separation of the diastereomers is carried out.

The processes according to the invention are intended to be illustrated by way of example by process [A] in the following reaction scheme:

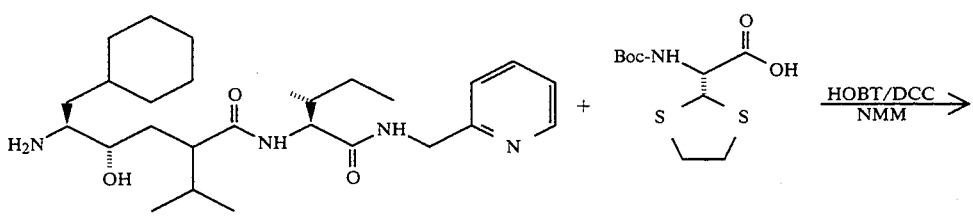

[A]

-continued

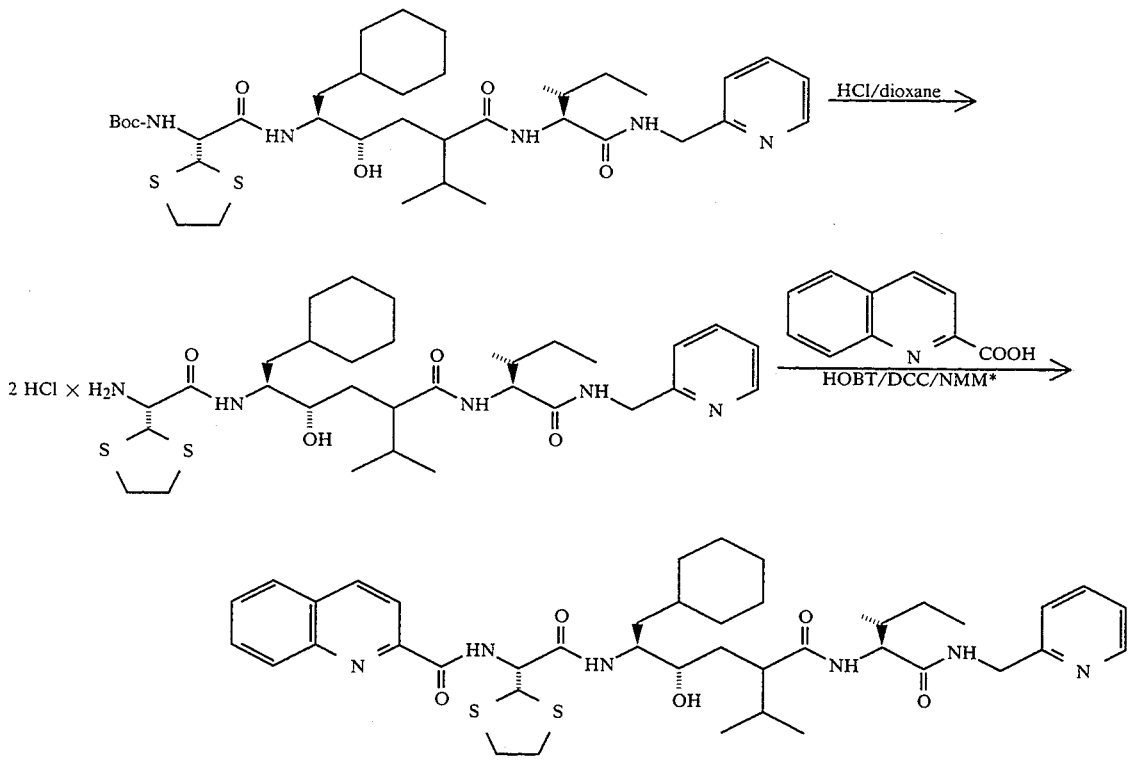

Suitable solvents are the customary organic solvents which do not change under the reaction conditions. These preferably include organic solvents such as alcohols, for example methanol, ethanol or n-propanol, ethers, for example diethyl ether, glycol monomethyl ether or glycol dimethyl ether, dioxane or tetrahydrofuran, or hydrocarbons such as benzene, toluene, xylene, cyclohexane or mineral oil fractions, or halogenohydrocarbons such as methylene chloride, dichloroethane (DCE), chloroform, carbon tetrachloride, or dimethyl sulphoxide, dimethylformamide, hexamethylphosphoramide, ethyl acetate, pyridine, triethylamine or picoline. It is also possible to use mixtures of the solvents mentioned. Dichloromethane, dichloroethane, dimethylformamide or n-propanol are particularly preferred.

Auxiliaries which may be employed for the respective peptide couplings are preferably condensing agents, which can also be bases, in particular if the carboxyl group is present in activated form as an anhydride. The customary condensing agents such as carbodiimides, for example N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride, or carbonyl compounds such as carbonyldiimidazole, or 1,2-oxazolium compounds such as 2-ethyl-5-phenyl-1,2-oxazolium-3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or benzotriazolyloxy-tri(dimethylamino)phosphonium hexafluorophosphate, or 1-hydroxybenzotriazole are employed here and alkali metal carbonates, for example sodium carbonate or potassium carbonate, or sodium hydrogen carbonate or potassium hydrogen carbonate, or organic bases such as trialkylamines, for example triethylamine, N-ethylmorpholine, N-methylpiperidine or diisopropylethylamine, are employed as bases. Dicyclohexylcarbodiimide, N-methylmorpholine and 1-hydroxybenzotriazole are particularly preferred.

The amino protective group is removed in a manner known per se under acidic or basic conditions, or reductively by catalytic hydrogenation, for example using Pd/C in organic solvents such as ethers, for example tetrahydrofuran or dioxane, or alcohols, for example methanol, ethanol or isopropanol.

The reactions are in general carried out in a temperature range from $-20°$ C. to $+80°$ C. preferably from $0°$ C. to $+60°$ C.

In general, the reaction is carried out at normal pressure. However, it is also possible to work at reduced pressure or at elevated pressure (for example from 0.5 to 5 bar).

The compounds of the general formula (VIII) are known per se and can be prepared by reaction of an appropriate fragment, consisting of one or more amino acid groups, having a free carboxyl group, if appropriate present in activated form, with a complementary fragment, consisting of one or more amino acid groups, if appropriate in activated form, and by repeating this process with appropriate fragments [cf. here EP 300 189 and H. Bühlmayer et al., *J. Med. Chem.* 31, 1839 (1988)]; protective groups can then optionally be removed or replaced by other protective groups [cf. Houben-Weyl, Methoden der organischen Chemie (Methods of organic chemistry), Synthese von Peptiden (Synthesis of peptides) II, 4th ed. vol. 15/1, 15/2, Georg Thieme Verlag, Stuttgart].

Auxiliaries employed for the introduction of the radical W' (V)/(VIII) are the condensing agents mentioned above under the peptide coupling.

The removal of the amino protective groups can also be carried out by a customary method using acids, such as, for example, hydrochloric acid or trifluoroacetic acid.

The compounds of the general formula (III) are known per se and can be prepared in analogy to the methods published in EP 437 729 and EP 432 595 [cf. here additionally D. J. Plata et al., THL 32, 3623 (1991) and J. P. Vacca et al., J. Med. Chem. 34, 1228 (1991)].

The compounds of the general formulae (IV), (VI) and (VII) are known in some cases or are new and can be prepared by introducing the amino protective group $R^{13}$ (see formula IV) into compounds of the general formula (IX)

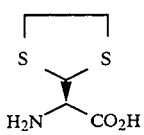

(IX)

if appropriate with activation using reagents, such as, for example, $(R^{13}O\text{—}CO)_2O$, $R^{13}\text{—}O\text{—}CO\text{—}Cl$ or $(R^{13}\text{—}O\text{—}CO)O\text{—}N\text{—}$ succinimide, in one of the above-mentioned solvents/solvent mixtures, preferably dioxane/$H_2O$ using sodium hydroxide or in dioxane using triethylamine, and in the case of the compounds of the general formulae (VI) and (VII) first removing the protective group $R^{13}$, as described above, and in the sense of a peptide coupling as described above introducing the radicals W'—A'—B—OH or $R^{13}$—A'—B'—OH, in which W', A', B' and $R^{13}$ have the above-mentioned meaning, likewise as described above.

The reactions proceed in a temperature range from 0° to +50° C., preferably at room temperature and normal pressure.

The compound of the general formula (IX) is (as a mixture) known [cf. M. P. Mertes, A. A. Ramsey, J. Med. Chem. 1.2., 342 (1969)].

The compounds of the general formula (V) are known.

The inhibitors described here are inhibitors of HIV protease and as such can be employed for all purposes for which enzyme inhibitors are suitable. This is, for example, the use in diagnosis to improve the precision and selectivity of enzyme activity measurements. In affinity chromatography, they can be used as affinity labels and in research they can be used for the elucidation of reaction mechanisms and the specificity of enzymatic reactions.

Moreover, it has surprisingly been found that the compounds of the general formula (I) have an extremely potent action against retroviruses. This is confirmed by an HIV-specific protease enzyme test.

The results of the examples listed below were determined by the HIV test system described in the following references [cf. Hansen, J., Billich, S., Schulze, T., Sukrow, S. and Mölling, K. (1988), EMBO Journal, Vol. 7, No. 6, pp. 1785-1791]: purified HIV protease was incubated with synthetic peptide which imitates a cleavage site in the Gag precursor protein and represents an in vivo cleavage site of the HIV protease. The resulting cleavage products of the synthetic peptide were analysed by means of reverse phase high performance liquid chromatography (RP-HPLC). The $IC_{50}$ values given relate to the substance concentration which causes a 50% strength inhibition of the protease activity under the above-mentioned test conditions.

Enzyme assay, HIV-1

TABLE I

| Ex. no. | $IC_{50}$ (RP-HPLC) (M) HIV-1 |
| --- | --- |
| 1 | 1.4–9 |
| 2 | 1.3–9 |
| 3 | 1.3–8 |
| 4 | 1.6–8 |
| 5 | 1.4–9 |
| 8 | 1.2–9 |
| 9 | 1.0–9 |
| 10 | 6.8–8 |
| 11 | 1.4–10 |
| 12 | 9.8–8 |
| 13 | 6.4–11 |
| 14 | 1.3–10 |
| 15 | 6.8–9 |
| 16 | 2.1–8 |
| 18 | 1.9–9 |
| 19 | 2.3–8 |
| 20 | 1.6–8 |
| 21 | 8.7–9 |

The compounds according to the invention additionally exhibited action in lentivirus-infected cell cultures. This could be shown by the example of the HIV virus.

HIV infection in cell culture

The HIV test was carried out with slight modifications by the method of Pauwels et al. [cf. Journal of Virological Methods 20, (1988), 309-321].

Normal human blood lymphocytes (PBLs) were enriched on Ficoll-Hypaque and stimulated in RPMI 1640, 20% foetal calf serum containing phytohaemagglutinin (90 µg/ml) and interleukin-2 (40 U/ml). For infection with the infectious HIV, PBLs were pelleted and the cell pellet was then suspended in 1 ml of HIV virus adsorption solution and incubated for 1 hour at 37° C.

The virus adsorption solution was centrifuged and the infected cell pellet taken up in growth medium so that a concentration of $1 \times 10^5$ cells per ml was established. The cells infected in such a way were pipetted at $1 \times 10^4$ cells/well into the wells of 96-well microtitre plates.

The first vertical row of the microtitre plate contained only growth medium and cells which had not been infected, but otherwise had been treated exactly as described above (cell control). The second vertical row of the microtitre plate contained only HIV-infected cells (virus control) in growth medium. The other wells contained the compounds according to the invention in different concentrations, starting from the wells of the 3rd vertical row of the microtitre plate, from which the test substances were diluted $2^{10}$ times in steps of two.

The test batches were incubated at 37° C. until in the untreated virus control the syncytia formation typical of HIV occurred (between day 3 and 6 after infection), which was then assessed by microscopy. Under these test conditions, about 20 syncytia resulted in the untreated virus control, while the untreated cell control contained no syncytia.

The $IC_{50}$ values were determined as the concentrations of the treated and infected cells at which 50% (about 10 syncytia) of the virus-induced syncytia were suppressed by the treatment with the compound according to the invention.

It has now been found that the compounds according to the invention protect HIV-infected cells from virus-induced cell destruction.

TABLE II

| Ex. No. | IC$_{50}$ ($\mu$M) [PBL] | [H-9] |
|---|---|---|
| 1 | >1 | |
| 2 | 10 | |
| 3 | 1 | |
| 4 | 1 | |
| 5 | 0.4 | |
| 8 | 1 | |
| 9 | 0.04 | 0.011 |
| 10 | 5 | |
| 11 | 1 | |
| 12 | 5 | |
| 13 | 0.05 | 0.038 |
| 14 | >1 | |
| 15 | 10 | |
| 16 | 10 | |
| 18 | 0.4 | |
| 19 | <0.08 | |
| 20 | <0.4 | |
| 21 | <0.4 | |

The compounds according to the invention are useful active compounds for the treatment and prophylaxis of diseases produced by retroviruses, in human and veterinary medicine.

Indication areas which can be mentioned in human medicine are, for example:

1.) The treatment and prophylaxis of human retrovirus infections.
2.) For the treatment or prophylaxis of HIV I (human immunodeficiency virus; formerly called HTLV III/LAV) and diseases (AIDS) and the stages associated with it such as ARC (AIDS-related complex) and LAS (lymphadenopathy syndrome) caused by HIV II, as well as the immunodeficiency and encephalopathy caused by this virus.
3.) For the treatment or the prophylaxis of an HTLV-I or HTLV-II infection.
4.) For the treatment or prophylaxis of the AIDS-carrier state (AIDS-transmitter state).

Indications which can be mentioned in veterinary medicine are, for example:

Infections with
a) maedi-visna (in sheep and goats)
b) progressive pneumonia virus (PPV) in sheep and goats
c) caprine arthritis encephalitis virus (in sheep and goats)
d) zwoegerziekte virus (in sheep)
e) infectious anaemia virus (of the horse)
f) infections caused by the feline leukaemia virus
g) infections caused by the feline immunodeficiency virus (FIV)
h) infections caused by the simian immunodeficiency virus (SIV)

The above-mentioned items 2, 3 and 4 are preferred from the indication area in human medicine.

The present invention includes pharmaceutical preparations which, in addition to non-toxic, inert pharmaceutically suitable excipients contain one or more compounds of the formula (I) or consist of one or more active compounds of the formula (I), and processes for the production of these preparations.

The active compounds of the formula (I) should preferably be present in the above-mentioned pharmaceutical preparations in a concentration of about 0.1 to 99.5, preferably of about 0.5 to 95, % by weight of the total mixture.

The above-mentioned pharmaceutical preparations can also contain other pharmaceutical active compounds in addition to the compounds of the formula (I).

The above-mentioned pharmaceutical preparations are prepared in a customary manner by known methods, for example by mixing the active compound or compounds with the excipient or excipients.

In general, it has proven advantageous both in human and in veterinary medicine to add the active compound or compounds according to the invention in total amounts of about 0.5 to about 500, preferably 1 to 100, mg/kg of body weight every 24 hours, if appropriate in the form of several individual doses, to achieve the desired results. An individual dose contains the active compound or compounds preferably in amounts of about 1 to about 80, in particular 1 to 30, mg/kg of body weight. However, it may be necessary to deviate from the doses mentioned, in particular depending on the nature and the body weight of the subject to be treated, the nature and the severity of the disease, the type of preparation and administration of the medicament and the period or interval within which administration takes place.

APPENDIX TO THE EXPERIMENTAL SECTION

I. List of the eluent mixtures used for chromatography:

I dichloromethane:methanol
II toluene:ethyl acetate
III acetonitrile:water
IV dichloromethane:tetrahydrofuran
V toluene:acetonitrile II. Amino acids In general, the configuration is designated by placing an L or D before the amino acid abbreviation, in the case of the racemate a D,L-, where for simplification in the case of L-amino acids the designation of configuration can be omitted and an explicit designation is then only carried out in the case of the D-form or of the D,L-mixture.

| Ala | L-alanine |
|---|---|
| Arg | L-arginine |
| Asn | L-asparagine |
| Asp | L-aspartic acid |
| Cys | L-cysteine |
| Gln | L-glutamine |
| Glu | L-glutamic acid |
| Gly | L-glycine |
| His | L-histidine |
| Ile | L-isoleucine |
| Leu | L-leucine |
| Lys | L-lysine |
| Met | L-methionine |
| Pro | L-proline |
| Phe | L-phenylalanine |
| Ser | L-serine |
| Thr | L-threonine |
| Trp | L-tryptophan |
| Tyr | L-tyrosine |
| Val | L-valine |

III. Abbreviations

| z | benzyloxycarbonyl |
|---|---|
| Boc | tert-butoxycarbonyl |
| CMCT | 1-cyclohexyl-3-(2-morpholino-ethyl)- |

| | |
|---|---|
| | carbodiimide-metho-p-toluenesulphonate |
| DCC | dicyclohexylcarbodiimide |
| DMF | dimethylformamide |
| HOBT | 1-hydroxybenzotriazole |
| Ph | phenyl |
| THF | tetrahydrofuran |
| Cha | cyclohexylalanine |
| Aib | 2-amino-2-methylpropionic acid |
| NMM | N-methylmorpholine |

PREPARATION EXAMPLES

Example 1

1-{(2R,S,4S,5S)
-5-[(2R)-N-(tert-Butoxycarbonyl)-2-amino-2-[2-(1,3-dithiolan-2-yl)]ethanoyl]amino-6-cyclohexyl-4-hydroxy-2-(1-methyl)ethyl-hexanoyl}-S-isoleucinyl2-pyridylamide A stirred solution, cooled to 0° C. of 614 mg (2.20 mmol) of (2R)-N-(tert-butoxycarbonyl)-2-amino-2-[2-(1,3-dithiolan-2-yl)]acetic acid (EP 412 350) and 337 mg (2.20 mmol) of HOBT in 10 ml of anhydrous dichloromethane is treated with 434 mg (2.10 mmol) of DCC and the mixture is stirred for 5 min. A solution of 1.10 g (2.20 mmol) of 1-{(2R,S,4S,5S)-[5-amino-6-cyclohexyl-4-hydroxy-2-(1-methyl)ethyl-hexanoyl]}-S-isoleucinyl-2-pyridylmethylamide dihydrochloride [EP 437 729] and 0.88 ml (8.0 mmol) of N-methylmorpholine in 10 ml of dichloromethane is then added dropwise. The cooling bath is removed and the reaction mixture can be stirred at room temperature for 2 h. The end of the reaction is determined by thin layer chromatography. The resulting urea is removed by filtration, the filtrate is concentrated in vacuo and the crude product is purified by chromatography on 90 g of silica gel (dichloromethane:methanol 95:5). 1.29 g (88% of theory) of the title compound are obtained as a pale powder.

Melting point: 252° C. (dec.) $R_f=0.19, 0.23$, I (9:1)
MS (FAB): m/e=736 (M+H)+

Example 2

1-{(2R,S;4S,5S)-5-[(2R)-2-Amino-2-[2-(1,3-dithiolan-2-yl)]ethanoyl]-amino-6-cyclohexyl-4-hydroxy-2-(1-methyl)ethyl-hexanoyl}-S-isoleucinyl-2-pyridylamide dihydrochloride

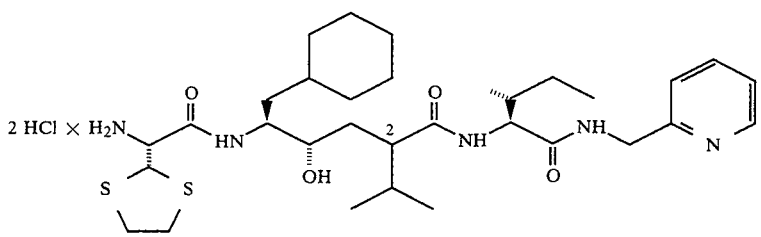

A solution of 2.41 g. (3.28 mmol) of the compound from Example 1 in 17 ml of a 4N solution of gaseous hydrogen chloride in anhydrous dioxane is stirred at 0° C. for 30 min. 15 ml of toluene are then added and the mixture is concentrated in vacuo. This process is repeated a further two times, and the residue is then triturated with ether, filtered off with suction and dried in a high vacuum over KOH. 2.29 g (98% of theory) of the title compound are obtained as a colourless powder.

Melting point: from 192° C. (dec.) $R_f=0.47$ III(9:1)
MS (FAB): m/e=636 (M+H)+

Example 3 and Example 4

1-{(2R,4S,5S)-5-[(2R)-N-(tert-Butoxycarbonyl)-2-amino-2-[2-(1,3-dithiolan-2-yl)]ethanoyl]amino-6-cyclohexyl-4-hydroxy-2-(phenyl)methyl-hexanoyl}-S-isoleucinyl-2-pyridylamide

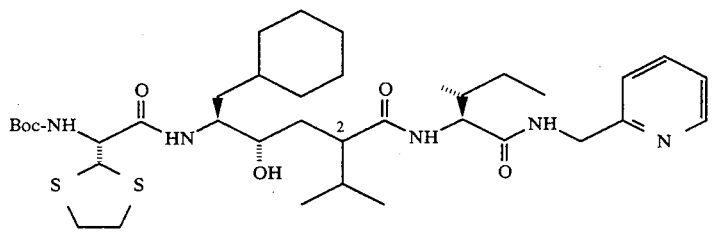

(Example 3)

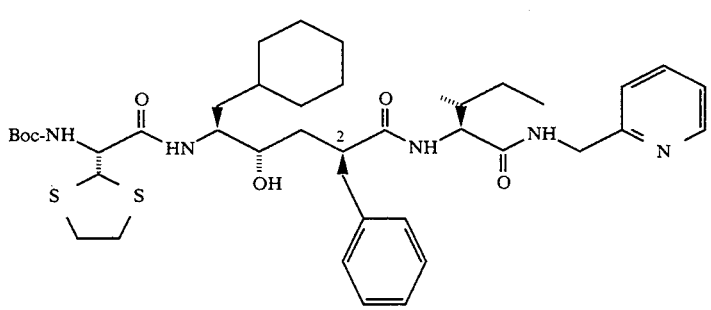

1-{(2S,4S,5S)-5-[(2R)-N-(tert-Butoxycarbonyl)-2-amino-2-[2-(1,3-dithiolan-2-yl)]ethanoyl]amino-6-cyclohexyl-4-hydroxy-2-(phenyl)methyl-hexanoyl}-S-isoleucinyl2-pyridylamide

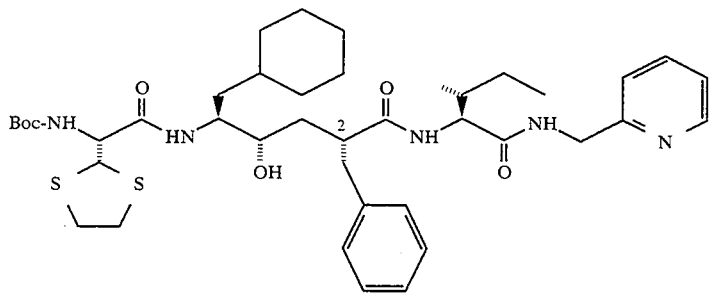

As described for Example 1, starting from 258 mg (0.92 mmol) of (2R)-N-(tert-butoxycarbonyl)-2-amino-2-[2-(1,3-dithiolan-2-yl)]acetic acid [EP 412 350] and 500 mg (0.84 mmol) of 1-{(2R,S,4S,5S)-[5-amino-6-cyclohexyl-4-hydroxy-2-(phenyl)methyl-hexanoyl]-S-isoleucinyl-2-pyridylmethylamide dihydrochloride (prepared according to EP 437 729] and by chromatography of the crude product on 20 g of silica gel (eluent mixture I, 95:5), 593 mg (90%) of the title compound are obtained as a mixture of the 2(R,S)-diastereomers. By chromatographic separation on 80 g of silica gel, 217 mg (33%) of the non-polar (2R)-isomer are obtained as an amorphous powder (Example 3).

As described for Example 1, starting from 249 mg (0.89 mmol) of (2R)-N-(tert-butoxycarbonyl)-2-amino-2-[2-(1,3-dithiolan-2-yl)]acetic acid [EP 412 350] and 440 mg (0.81 mmol) of 1-{(2R,S,4S,5S)-[5-amino-6-cyclohexyl-4-hydroxy-2-(2-propenyl)-hexanoyl]}-S-

(Example 4)

isoleucinyl-2-pyridylmethylamide dihydrochloride [prepared according to EP 437 729] and by chromatography of the crude product on 24 g of silica gel (eluent mixture I, 9:1), 553 mg (93%) of the title compound are obtained as a pale powder (mixture of the 2 R,S-diastereomers). R$_f$=0.48, 0.42 (I, 9:1) MS (FAB): m/e=734 (M+H)+

Example 6

1-{(2R,S,4S,5S)-5-[(2R)-2-Amino-2-[2-(1,3-dithiolan-2-yl)]ethanoyl]amino-6-cyclohexyl-4-hydroxy-2-(phenyl)methyl-hexanoyl}-S-isoleucinyl-2-pyridylamide dihydrochloride

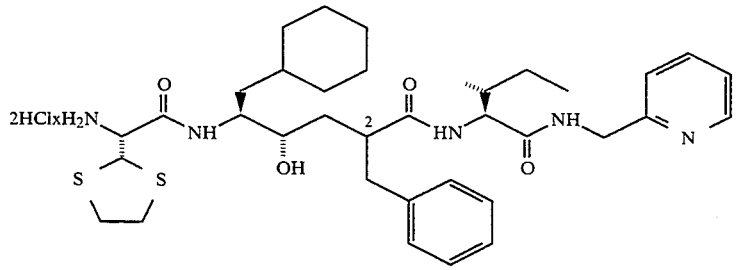

Example 3: R$_f$=0.65, I(9:1) Example 3: MS (FAB): m/e=784 (M+H)+Example 4: 257 mg (39%) as crystals Example 4: melting point 201° C. Example 4: R$_f$=0.51, I(9:1) Example 4: MS (FAB): m/e=784 (M+H)+

Example 5

1-{(2R,S,4S,5S)-5-[(2R)-N-(tert-Butoxycarbonyl)-2-amino-2-[2-(1,3-dithiolan-2-yl)]ethanoyl]amino-6-cyclohexyl-4-hydroxy-2-(2-propenyl)-hexanoyl}-S-isoleucinyl-2-pyridylamide As described for Example 2, starting from 589 mg (0.75 mmol) of the compound from Example 3/4 (mixture of the 2(R,S)-diastereomers), 484 mg (86%) of the title compound are obtained as a colourless powder. R$_f$=0.29, 0.34, (I, 9:1) MS (FAB): m/e=684 (M+H)+

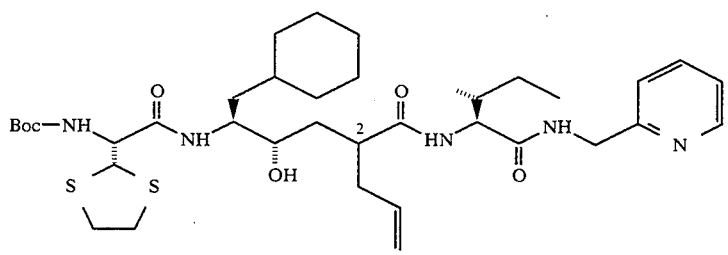

Example 7

1-{(2R,S,4S,5S)-5-[(2R)-2-Amino-2-[2-(1,3-dithiolan-2-yl)]ethanoyl]amino-6-cyclohexyl-4-hydroxy-2-(2-propenyl)hexanoyl}-S-isoleucinyl-2-pyridylamide

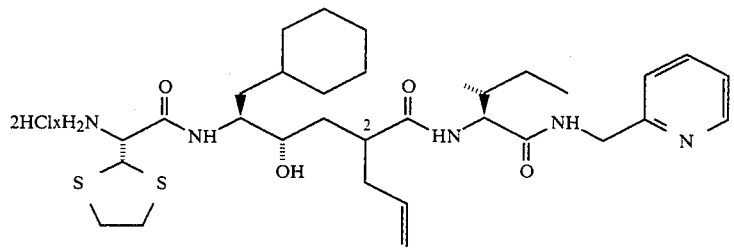

As described for Example 2, starting from 560 mg (0.91 mmol) of the compound from Example 5, 452 mg (91%) of the title compound are obtained as a colourless powder. $R_f$=0.08, III (9:1) MS (FAB): m/e=473 (M+H)+

Example 8 and Example 9

1-{(2R,4S,5S)-5-[(2S)-3-(tert-Butylsulphonyl)-2-(1-naphthylmethyl)propanoyl]-(2R)-N-(tert-butoxycarbonyl)-2-amino-2-[2-(1,3-dithiolan-2-yl)ethanoyl]amino-6-cyclohexyl-4-hydroxy-2-(1-methyl)ethyl-hexanoyl}-S-isoleucinyl-2-pyridylamide thyl)propionic acid [prepared according to H. Bühlmayer et al., *J. Med. Chem.* 31, 1839 (1988)] and 0.40 g (2.64 mmol) of HOBT in 20 ml of anhydrous dichloromethane is treated with 0.52 g (2.52 mmol) of DCC and stirred for 5 min. A solution of 1.55 g (2.19 mmol) of the compound from Example 2 and 0.96 ml (8.74 mmol) of N-methylmorpholine in 30 ml of dichloromethane is then added dropwise and the reaction can be stirred at room temperature for 2 h. The resulting urea is removed by filtration, the filtrate is concentrated in vacuo and the crude product is purified by chromatography on 360 g of silica gel (dichloromethane: methanol 95:5). 586 mg (28% of theory) of the non-polar (2R)-isomer are obtained as a colourless powder (Example 8)

Melting point: from 209° C. (dec.) $R_f$=0.20, I (95:5) MS (FAB): m/e=952 (M+H)+and 690 mg (33%) of the polar (2S)-isomer as a colourless powder (Example 9)

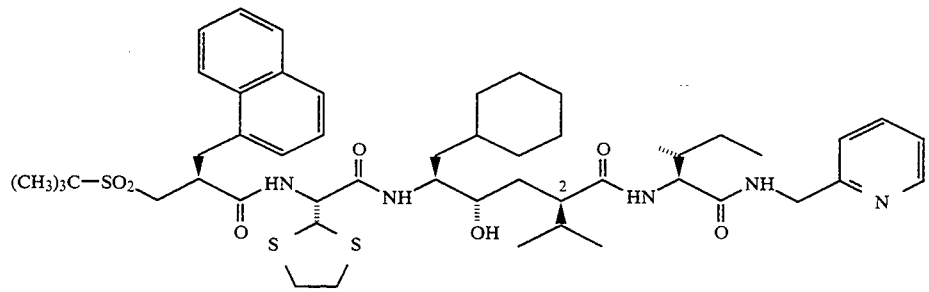

1-}(2S,4S,5S)-5-[(2S)-3-(tert-Butylsulphonyl)-2-(1-naphthylmethyl)propanoyl]-(2R)-N-(tert-butoxycarbonyl)-2-amino-2-[2-(1,3-dithiolan-2-yl)]ethanoyl]amino-6-cyclohexyl-4-hydroxy-2-(1-methyl)ethyl-hexanoyl}-S-isoleucinyl-2-pyridylamide Melting point: 233° C. (dec.) $R_f$=0.14, I (95:5) MS (FAB): m/e=952 (M+H)+

As described for Examples 8 and 9, the products listed in Table 1 are obtained by coupling the appropriate acids with the amine hydrochlorides (starting materials):

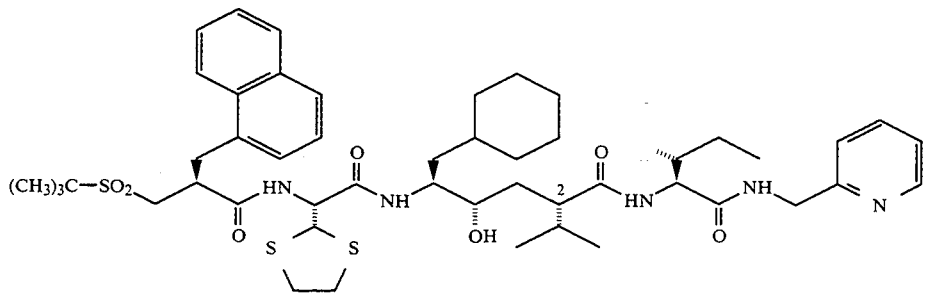

A stirred solution, cooled to 0° C. of 0 80 g (2.40 mmol) of (2S)-3-tert-butylsulphonyl-2-(1-naphthylme- TABLE 1
| Ex. No. | W—A—B— | R³ | Yield (%) | MS (FAB) m/e (M+H)+ | Rf/eluent ratio | Melting point: (°C.) | Starting material from Ex. |
|---|---|---|---|---|---|---|---|
| 10 | 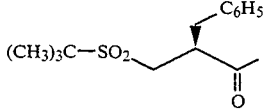 | (R)-CH(CH$_3$)$_2$ | 13 | 902 | 0.30,I(95:5) | 133 | 2 |
| 11 | 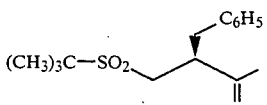 | (S)-CH(CH$_3$)$_2$ | 22 | 902 | 0.26,I(95:5) | 129 | 2 |
| 12 | 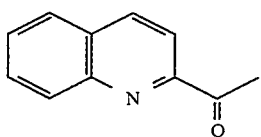 | (R)-CH(CH$_3$)$_2$ | 27 | 791 | 0.18,I(95:5) | 214 | 2 |
| 13 | 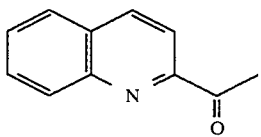 | (S)-CH(CH$_3$)$_2$ | 39 | 791 | 0.11,I(95:5) | 232 | 2 |
| 14 | 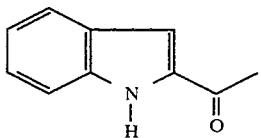 | (R,S)-CH(CH$_3$)$_2$ | 46 | 779 | 0.17,IV(4:1) | 164 | 2 |
| 15 | 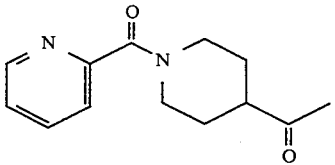 | (R)-CH(CH$_3$)$_2$ | 13 | 852 | 0.19,III(95:5) | amorphous | 2 |
| 16 | 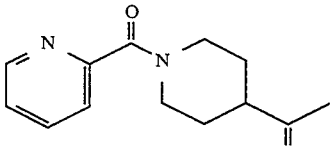 | (S)-CH(CH$_3$)$_2$ | 34 | 852 | 0.14,III(95:5) | 252 | 2 |
| 17 | 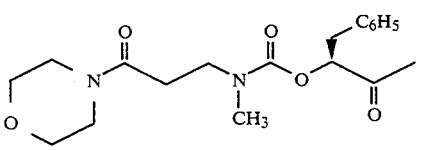 | (R)-CH(CH$_3$)$_2$ | 19 | 982 | 0.16,I(95:5) | amorphous | 2 |
| 18 | 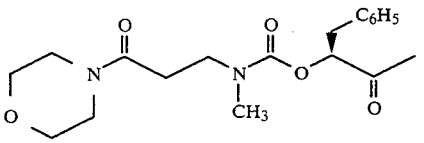 | (S)-CH(CH$_3$)$_2$ | 25 | 982 | 0.32,I(9:1) | 178 | 2 |
| 19 | 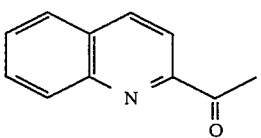 | (R,S)—H$_2$C | 35 | 789 | 0.17,V(1:1) | 194 | 7 |

TABLE 1-continued

| Ex. No. | W—A—B— | $R^3$ | Yield (%) | MS (FAB) m/e (M+H)+ | $R_f$/eluent ratio | Melting point: (°C.) | Starting material from Ex. |
|---|---|---|---|---|---|---|---|
| 20 | 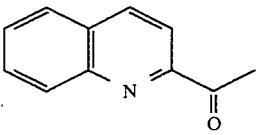 | (R)-CH$_2$—C$_6$H$_5$ | 23 | 839 | 0.37,V(1:1) | amorphous | 6 |
| 21 | 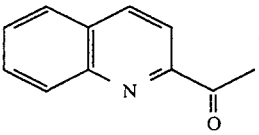 | (S)-CH$_2$—C$_6$H$_5$ | 41 | 839 | 0.26,V(1:1) | 112 | 6 |

We claim:
1. Compounds of the general formula (I)

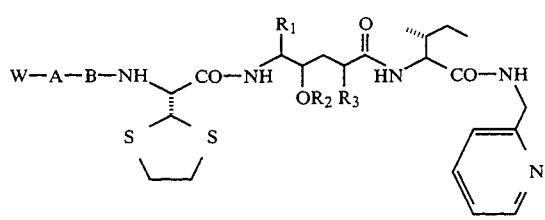

in which
W represents hydrogen or a typical amino protective group, or represents a group of the formula $R^4$—CO—,
in which
$R^4$ denotes quinolyl, indolyl, pyridyl, morpholino or piperazinyl, or denotes a radical of the formula

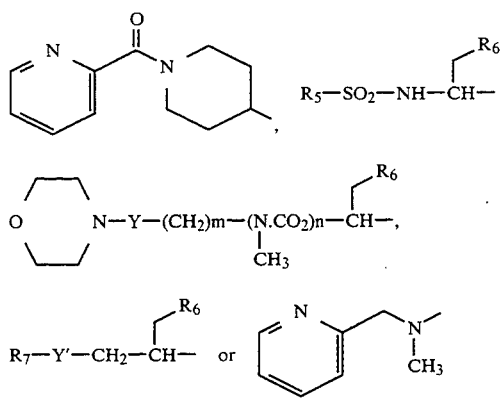

in which
$R^5$ denotes straight-chain or branched alkyl having up to 14 carbon atoms, which is optionally substituted by phenyl or naphthyl, or denotes benzyloxy or aryl having 6 to 10 carbon atoms, which is in turn substituted by alkyl having up to 4 carbon atoms, or denotes morpholino or pyrrolidinyl bonded via N,
$R^6$ denotes phenyl or naphthyl,
$R^7$ has the above-mentioned meaning of $R^5$ but does not represent morpholino or pyrrolidinyl bonded via N,
Y and Y' independently of one another denote the CO or SO$_2$ group,
m denotes a number 0, 1 or 2,
n denotes a number 0 or 1,
A and B are identical or different and represent a direct bond or represent a radical of the formula

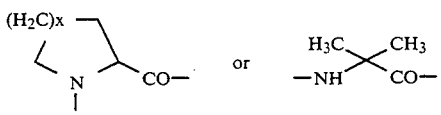

in which
x denotes the number 1 or 2 or
represent a group of the formula

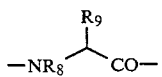

in which
$R^8$ denotes hydrogen or straight-chain or branched alkyl having up to 4 carbon atoms,
$R^9$ denotes cycloalkyl having 3 to 8 carbon atoms or aryl having 6 to 10 carbon atoms or hydrogen, or denotes straight-chain or branched alkyl having up to 8 carbon atoms, where the alkyl is optionally substituted by cyano, methylthio, hydroxyl, mercapto or guanidyl or by a group of the formula —NR$^{10}$R$^{11}$ or R$^{12}$—OC—,
in which
$R^{10}$ and $R^{11}$ independently of one another represent hydrogen, straight-chain or branched alkyl having up to 8 carbon atoms or phenyl, and
$R^{12}$ denotes hydroxyl, benzyloxy, alkoxy having up to 6 carbon atoms or the above-mentioned group —NR$^{10}$R$^{11}$, or the alkyl is optionally substituted by cycloalkyl having 3 to 8 carbon atoms or by aryl having 6 to 10 carbon atoms, which is in turn substituted by hydroxyl, halogen, nitro, alkoxy having up to 8 carbon atoms or by the group —NR$^{10}$R$^{11}$,
in which
$R^{10}$ and $R^{11}$ have the above-mentioned meaning, or the alkyl is optionally substituted by a 5- or 6-membered nitrogen-containing heterocycle or indolyl, in which the corresponding —NH functions are optionally protected by alkyl having up to 6 carbon atoms or by an amino protective group, R¹ represents straight-chain or branched alkyl having up to 3 carbon atoms, which is substituted by cyclohexyl or phenyl, R² represents hydrogen or straight-chain or branched alkyl having up to 4 carbon atoms, or represents a hydroxyl protective group, R³ represents straight-chain or branched alkyl or alkenyl each having up to 6 carbon atoms or represents benzyl, and their physiologically acceptable salts.

2. Compounds of the general formula (I) according to claim 1 in which

W represents hydrogen, tert-butoxycarbonyl (BOC), 9-fluorenylmethoxycarbonyl (Fmoc), benzyloxycarbonyl (Z) or pyridylmethoxycarbonyl, or represents a group of the formula R⁴—CO— in which R⁴ denotes quinolyl, indolyl, pyridyl, morpholino or piperazinyl, or denotes a radical of the formula

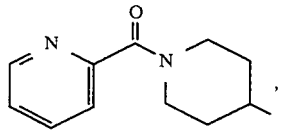

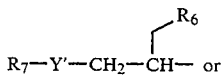

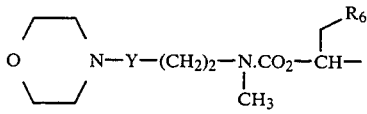

in which

Y and Y' independently of one another denote the CO or SO₂ group,

R⁶ denotes phenyl or naphthyl,

R⁷ denotes straight-chain or branched alkyl having up to 8 carbon atoms, tolyl, benzyloxy, phenyl or naphthyl, A and B independently of one another represent a direct bond or represent proline, alanine, arginine, aspartic acid, asparagine, glutamic acid, glutamine, histidine, leucine, methionine, threonine, tyrosine, cysteine, glycine, isoleucine, lysine, phenylalanine, serine, tryptophan or valine, R¹ represents benzyl or methylcyclohexyl, R² represents hydrogen, R³ represents straight-chain or branched alkyl or alkenyl each having up to 4 carbon atoms, or benzyl, and their physiologically acceptable salts.

3. Compounds of the general formula (I) according to claim 1, in which

W represents hydrogen or tert-butoxycarbonyl (BOC) or represents a group of the formula R⁴—CO—, in which R⁴ denotes quinolyl or indolyl, or denotes a radical of the formula

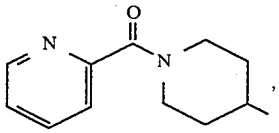

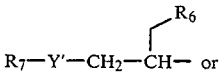

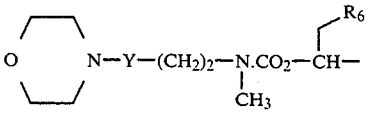

in which

R⁶ denotes phenyl or naphthyl,

R⁷ denotes straight-chain or branched alkyl having up to 4 carbon atoms, tolyl, benzyloxy, phenyl or naphthyl, Y and Y' independently of one another denote the CO or SO₂ group, A and B independently of one another represent a direct bond, or represent phenylalanine, R¹ represents benzyl or methylcyclohexyl, R² represents hydrogen, R³ represents straight-chain or branched alkyl having up to 3 carbon atoms, allyl or benzyl, and their physiologically acceptable salts.

* * * * *